United States Patent [19]

Mikhail

[11] Patent Number: 5,443,523
[45] Date of Patent: Aug. 22, 1995

[54] FEMORAL STEM CEMENT MANTLE

[76] Inventor: W. E. Michael Mikhail, 4203 Shamley Green, Toledo, Ohio 43623

[21] Appl. No.: 210,713

[22] Filed: Mar. 18, 1994

[51] Int. Cl.$^6$ .............................................. A61F 2/34
[52] U.S. Cl. ..................................... 623/23; 623/16; 623/18
[58] Field of Search ................... 623/23, 22, 16, 20, 623/18

[56] References Cited

U.S. PATENT DOCUMENTS

| | | | |
|---|---|---|---|
| Re. 32,488 | 9/1987 | Gustilo et al. | 623/23 |
| 3,793,650 | 2/1974 | Ling et al. | |
| 3,829,904 | 8/1974 | Ling et al. | |
| 3,924,274 | 12/1975 | Heimke et al. | 3/1.91 |
| 3,965,490 | 6/1976 | Murray et al. | 3/1.93 |
| 3,986,212 | 10/1976 | Sauer | 3/1.91 |
| 4,064,567 | 12/1977 | Burstein et al. | 3/1.91 |
| 4,279,042 | 7/1981 | Andriacchi et al. | 3/1.91 |
| 4,281,420 | 8/1981 | Raab | 3/1.91 |
| 4,336,618 | 6/1982 | Raab | 3/1.91 |
| 4,454,612 | 6/1984 | McDaniel et al. | 3/1.91 |
| 4,491,987 | 1/1985 | Park | 3/1.91 |
| 4,589,883 | 5/1986 | Kenna | 623/22 |
| 4,619,659 | 10/1986 | Witzel | 623/23 |
| 4,728,335 | 3/1988 | Jurgutis | 623/23 |
| 4,735,625 | 4/1988 | Davidson | 623/16 |
| 4,753,657 | 6/1988 | Lee et al. | 623/16 |
| 4,851,004 | 7/1989 | Homsy | 623/16 |
| 4,865,608 | 9/1989 | Brooker, Jr. | 623/23 |
| 4,881,536 | 11/1989 | Noble et al. | 606/94 |
| 4,888,023 | 12/1989 | Averill et al. | 623/23 |
| 4,904,267 | 2/1990 | Bruce et al. | 623/23 |
| 4,919,665 | 4/1990 | Homsy | 623/18 |
| 4,936,859 | 6/1990 | Morscher et al. | 623/18 |
| 5,078,746 | 1/1992 | Garner | 623/16 |
| 5,080,680 | 1/1992 | Mikhail et al. | 623/23 |
| 5,092,892 | 3/1992 | Ashby | 623/16 |
| 5,171,288 | 12/1992 | Mikhail et al. | 623/23 |
| 5,176,712 | 1/1993 | Homsy | 623/23 |
| 5,197,990 | 3/1993 | Lawes et al. | 623/23 |
| 5,290,318 | 3/1994 | Ling et al. | 623/23 |

FOREIGN PATENT DOCUMENTS

| | | |
|---|---|---|
| 0179626 | 4/1986 | European Pat. Off. . |
| 0243585A2 | 11/1987 | European Pat. Off. . |
| 2808740 | 9/1979 | Germany . |
| 3802214A1 | 7/1989 | Germany . |
| 9105872 | 5/1991 | Germany . |
| 1409053 | 10/1975 | United Kingdom . |
| 1409054 | 10/1975 | United Kingdom . |
| WO81/00670 | 3/1981 | WIPO . |

OTHER PUBLICATIONS

Article in *The Orthopedic Clinics of North America, Long-Term Results of Cemented Joint Replacement*, "Experience with Exeter Total Hip Replacement since 1970", by J. L. Fowler MB, FRCS et al., dated Jul. 1988, published by W. B. Saunders Company, at pp. 477–489.

Article in *The Orthopedic Clinics of North America, Long-Term Results of Cemented Joint Replacement*, "Mechanical Failure in the Femoral Component in Total Hip Replacement", by Gordon Bannister, M.Ch. Orth, FRCS, at pp. 567–573 dated Jul. 1988, published by W. B. Saunders Company.

Booklet entitled "The Exeter hip System—Seminar & Workshop" published by The University of Exeter, Exeter, England, in 1983 by A. J. C. Lee and R. S. M. Ling.

(List continued on next page.)

Primary Examiner—David Isabella
Assistant Examiner—Debra S. Brittingham
Attorney, Agent, or Firm—Emch, Schaffer, Schaub & Porcello

[57] ABSTRACT

A femoral stem prosthesis with a preapplied cement mantle having a design with elongated interstices configured to enhance the ability of additional bone cement to fully encapsulate those portions of the metal femoral stem intended to be within the cement mantle. A preformed cement mantle having elongated interstices may be preapplied to a femoral stem prosthesis.

3 Claims, 3 Drawing Sheets

OTHER PUBLICATIONS

Pp. 1 of brochure entitled "the SRN total hip Prosthesis". This was provided by the Examiner with the Office Action dated May 18, 1990 in application Ser. No. 07/480,229 filed Feb. 15, 1990 in which the Applicant herein is co-inventor.

Pp. 82–111 Proceedings of the Hip Society, 1980, Chapter 5, entitled "Total hip replacement using a collarless femoral prosthesis", by R. S. M. Ling.

Article entitled "Development of cemented HIP-stem shapes for optimal load transfer", by R. Huiskes and R. Boeklagen (date and publication unknown).

Catalog of Dow Corning Wright entitled "Whiteside Ortholoc© Modular Knee System–Total Condylar", 1989.

Catalog of DePuy, a Division of Boehringer Mannheim Corporation, entitled "The AMK ™ Total Knee System—Design Rationale and Surgical Procedure", 1988.

1987 Derwent Publications Ltd., Abstract of EP 243 585 A, Karp, 87-307965/44.

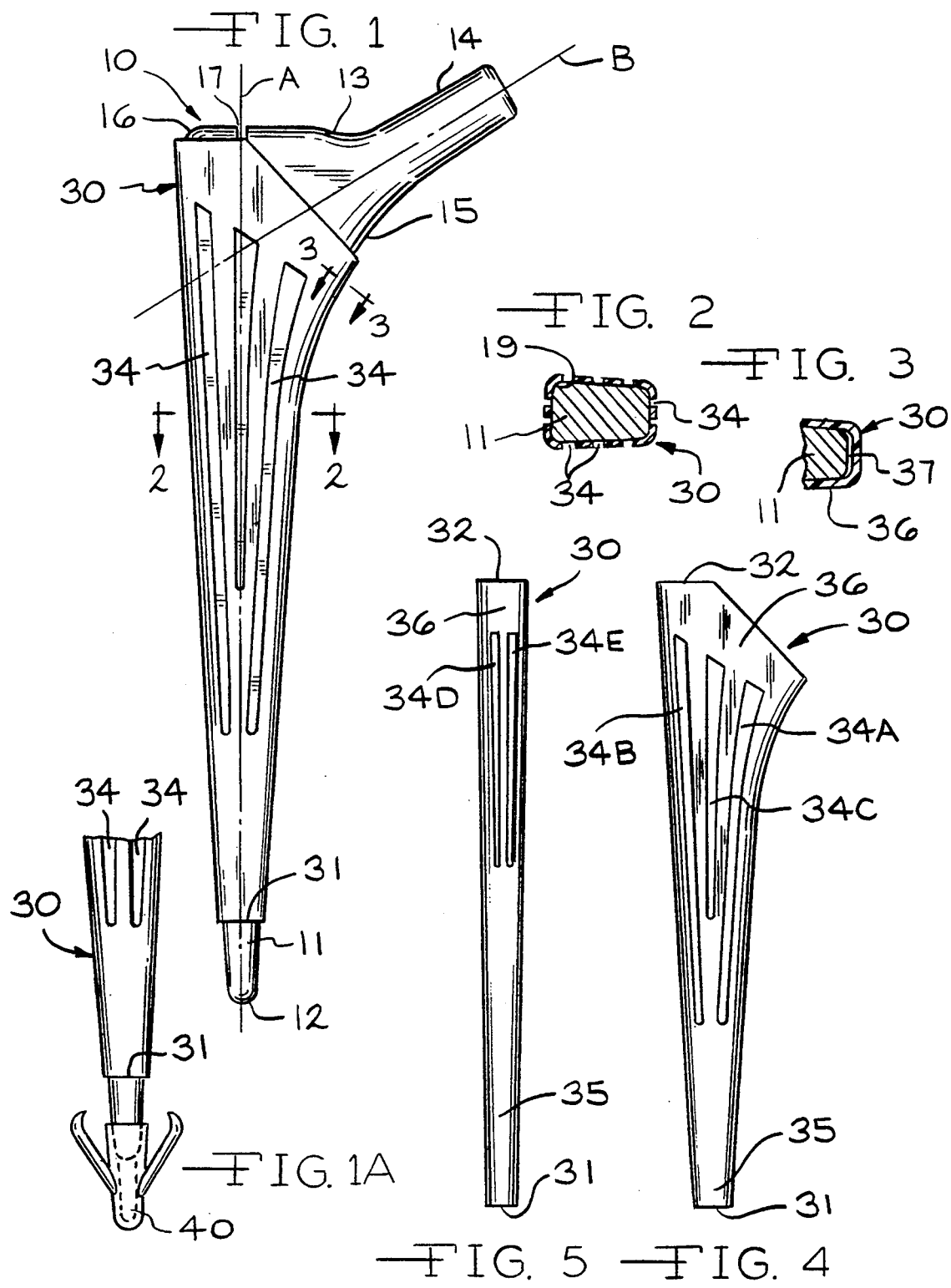

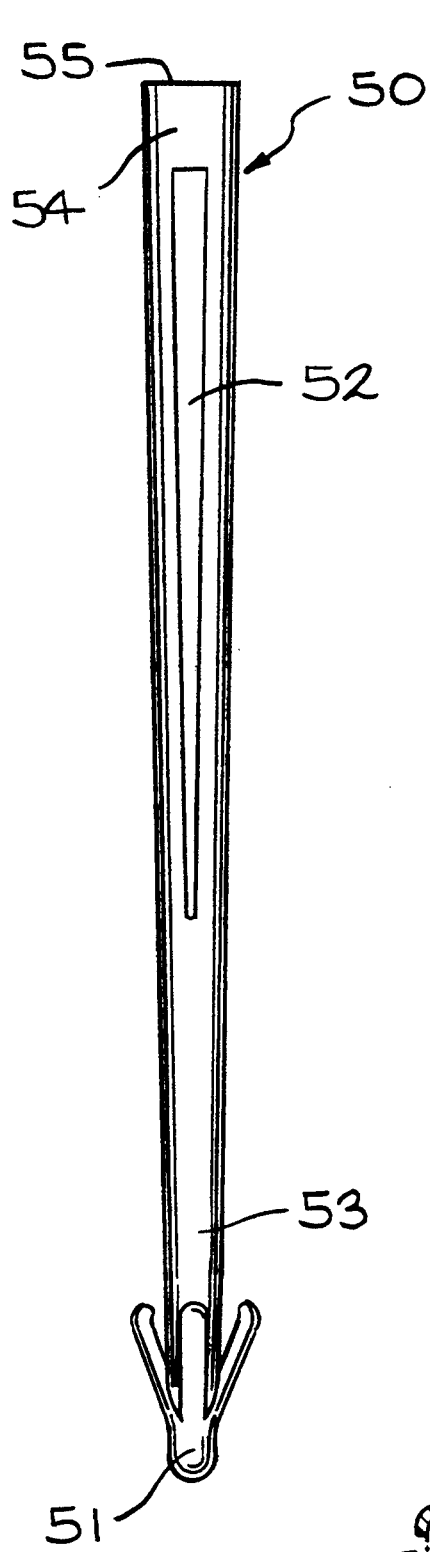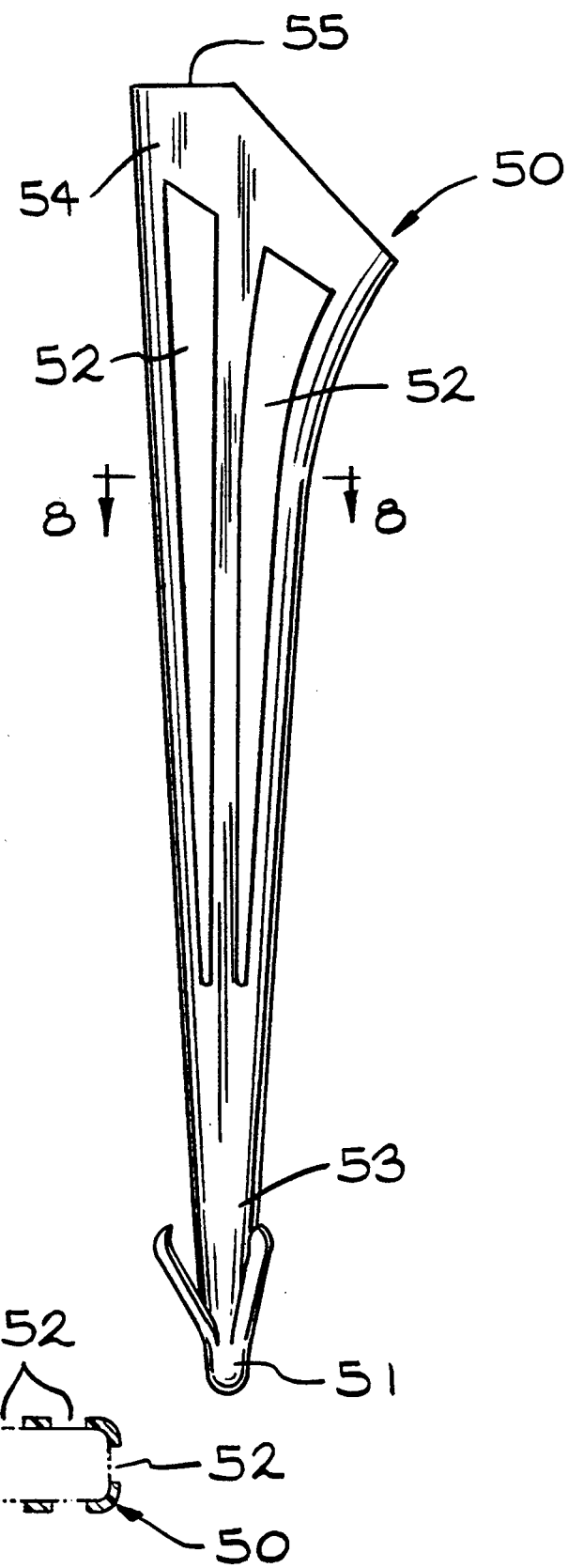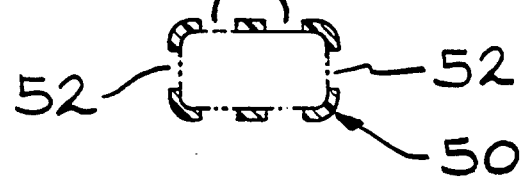

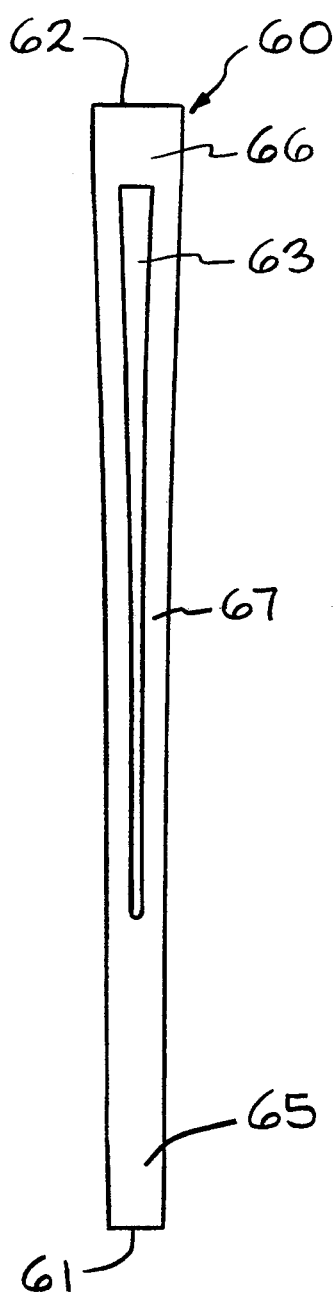
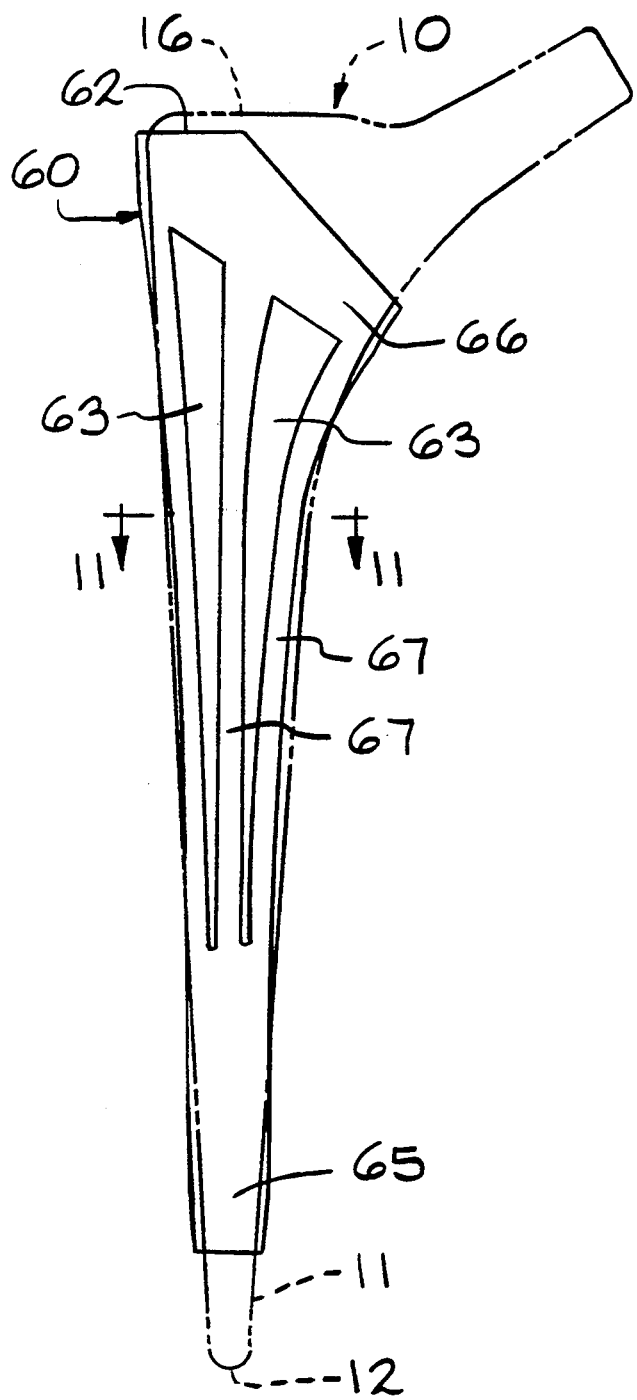
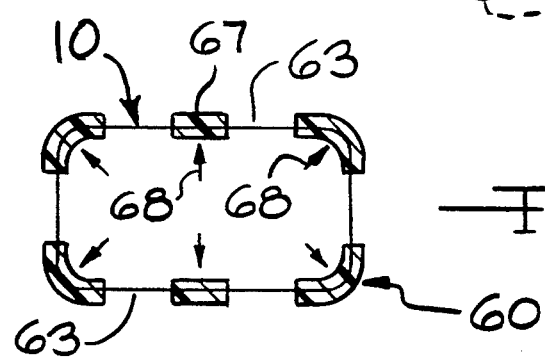

FEMORAL STEM CEMENT MANTLE

BACKGROUND ART

The present invention is an improvement upon the invention disclosed and claimed in U.S. Pat. No. 5,171,288, of which I am a coinventor and which is incorporated herein by reference. Such prior patent discloses a femoral stem prosthesis with preapplied cement mantle in which the cement mantle is provided with a series of interstices extending throughout the thickness of the preapplied cement mantle. The prosthesis is intended to be affixed in place by insertion into the femoral canal in which additional bone cement has been placed so that such additional cement will join with and become integrally connected to the preapplied cement mantle and will also flow into the interstices to engage the surface of the metal femoral stem component. It is desirable that upon insertion of the prosthesis into the femoral canal in which the additional cement has been placed that such additional cement completely fill the interstices as well as any gaps which may occur between the preapplied cement mantle and the surface of the metal femoral stem prosthesis. Thus, although the metal femoral stem prosthesis and the preapplied cement mantles are both manufactured to tight tolerances, it has been found that there may be gaps between the metal surface of the femoral stem prosthesis and the adjacent preapplied cement mantle. Where this occurs, it is desirable that the additional bone cement placed in the prepared cavity flow into such gaps as well as into the interstices in order that the metal femoral stem portion positioned therein is completely encapsulated by bone cement with no or at least an absolute minimum of voids.

DISCLOSURE OF INVENTION

The present invention is directed to a femoral stem prosthesis with a preapplied cement mantle and to a preformed cement mantle per se having a design which is specifically tailored to enhance the ability of the additional bone cement to fully encapsulate those portions of the metal femoral stem intended to be within the cement mantle and to permit such additional cement to flow completely into the interstices of the preapplied cement mantle and into any gaps occurring between the preapplied cement mantle and the surface of the metal femoral stem prosthesis.

The principle of a preapplied cement mantle may be used with different stems regardless of their geometry or cross-sectional configuration so long as it is tapered from the distal end to the proximal and regardless of the surface finish or the type of metal used, regardless of the offset or the neck-shaft angle of the prosthesis and regardless of whether the prosthesis is collared or collarless.

Accordingly, it is an object of the present invention to provide a femoral stem prosthesis with a preapplied cement mantle having a design permitting enhanced flow of bone cement into the interstices and any gaps between the preapplied cement mantle and the surface of the metal femoral stem prosthesis.

It is a further object of the present invention to provide a preapplied cement mantle having a design promoting complete encapsulation of the intended portions of the metal femoral stem prosthesis upon insertion in a prepared femoral canal and to minimize the possibility of voids occurring in the implanted prosthesis. The preapplied cement mantle may be provided as an integral part with the stem or as a separate envelope to be fitted during surgery; however, in either case there is no chemical or mechanical bonding between the cement envelope and the stem.

BRIEF DESCRIPTION OF THE DRAWINGS

FIG. 1 is an elevational view showing a femoral stem prosthesis with a preapplied cement mantle of the present invention positioned over the metal femoral stem portion thereof.

FIG. 1A is a fragmentary elevational view showing the preapplied cement mantle and femoral stem prosthesis in use with a centralizer.

FIG. 2 is a sectional view taken through line 2—2 of FIG. 1.

FIG. 3 is a fragmentary sectional view taken through line 3—3 of FIG. 1.

FIG. 4 is an elevational view of the preapplied cement mantle of the present invention.

FIG. 5 is a side elevational view of the preapplied cement mantle of the present invention as viewed from the left of FIG. 4.

FIG. 6 is an elevational view of a modified preapplied cement mantle according to the present invention.

FIG. 7 is a side elevational view of the preapplied cement mantle taken from the left of FIG. 6.

FIG. 8 is a sectional view taken through line 8—8 of FIG. 6.

FIG. 9 is an elevational view of another embodiment of preapplied cement mantle according to the present invention.

FIG. 10 is a side elevational view of the preapplied cement mantle taken from the left of FIG. 9.

FIG. 11 is a sectional view taken through line 11—11 of FIG. 9.

Best Mode of Carrying Out Invention

Referring now to FIGS. 1 and 2, there is shown a femoral hip joint prosthesis 10 having a stem 11 which is convergently tapered toward a distal end 12 and extending along a first axis of symmetry A to an area of juncture with a neck portion 13 lying on a second axis of symmetry B. Extending from the neck portion 13 is a frustoconically shaped Morse Taper Neck 14 to which may be attached a spherically shaped Morse Taper Head. The portion of the prosthesis joining the stem 11 to the neck 13 follows a smooth arcuate contour in the area 15 of the included angle between the respective axes of symmetry A and B. The portion of the femoral hip prosthesis 10 opposite the smooth arcuate portion 15, namely, that portion on the outside of the angle between the two axes of symmetry A and B, has an enlarged shoulder 16 in which is formed a dimple or recess 17 for driving the prosthesis into the femur. The stem 11 is tapered in both directions and has rounded corners 19. Additionally, the stem may be tapered mediolaterally with a slightly greater thickness on the left as viewed in FIG. 2.

Preferably, the femoral hip joint prosthesis 10 is formed of high-strength forged Co-Cr-Mo alloy (ASTM designation F-799 and has its surface polished to a high degree (also known as a color buff finish) to provide for a smoothness having a target surface roughness of four (4) microinches. However, the preapplied cement mantle of the present invention can be used with prostheses formed of other types of metal.

According to the present invention, a preapplied cement mantle 30 is provided having a design which enhances the ability of bone cement to completely fill the interstices and any gaps which may occur between the cement mantle and the metal surface of the stem 11. The preapplied cement mantle 30 is formed of polymethylmethacrylate (PMMA) or other commercially available bone cement or other biocompatible filling material. As shown in FIG. 1, when applied to the metal hip joint prosthesis, the preapplied cement mantle 30 extends from an area slightly spaced from the distal end 12 of the stem 11, in the range of 0.5 to 1.5 centimeters (cm), to an area up to the smooth arcuate portion 15 and the beginning of the enlarged shoulder 16. The preapplied cement mantle 30 has a substantially uniform thickness with the thickness being at least 0.7 mm and no thicker than about 2 mm.

As can be seen in the drawings, the preapplied cement mantle 30 extends from a distal end 31 spaced from the distal end 12 of the stem 11 to a proximal end 32. A series elongated generally triangular-shaped interstices 34 extend uninterrupted throughout a major area of the preapplied cement mantle 30. In the embodiment of FIGS. 1-4 there are provided a total of 10 interstices 34, three each on the side viewed in FIG. 4 and the side opposite and two each on the edge viewed in FIG. 5 and the edge opposite. As can be seen in FIG. 4, since the preapplied cement mantle follows a double taper from larger sizes at the proximal end 32 to smaller sizes at the distal end 31, the interstices 34 are also tapered and have larger sizes at the ends adjacent such proximal end 32 and rounded ends toward the distal end 31. Preferably, the interstices 34 have a width of at least 2 mm at the rounded ends adjacent the distal end 31. Additionally, as can be seen in FIGS. 4 and 5, some of the interstices, 34A and 34B, extend to a position closer to the distal end 31 than other of the interstices 34C, 34D and 34E. This, of course, is necessary as a result of the smaller circumference of the preapplied cement mantle 30 adjacent the distal end than the proximal end 32. However, at least some of the interstices 34 (for example 34A and 34B) have a length greater than one-half the distance of the length from the distal end 31 to the proximal end 32 and none of the interstices 34 extend completely to the distal end 31 or proximal end 32 so that there is a continuous circumferential band 35 of PMMA adjacent the distal end 31 and a continuous circumferential band 36 of PMMA adjacent the proximal end 32.

As may be seen in FIG. 1A, the preapplied cement mantle 30 may be utilized with a stem 11 to which a centralizer 40 has been affixed. Centralizers are well known in the art and, in and of themselves, form no part of the present invention.

Referring now to FIG. 3, there is shown a fragmentary portion of the metal stem 11 and the preapplied cement mantle 30 in the area of the band 36. As shown in FIG. 3, there is a small gap 37 between the preapplied cement mantle 30 and the stem 11. It is highly desirable that this gap 37 or any other gaps between the preapplied cement mantle 30 and the stem 11 be filled with PMMA upon insertion of the hip joint prosthesis 10 with the preapplied cement mantle applied thereto into a prepared femoral canal having bone cement positioned therein. The design of the preapplied cement mantle 30 of the present invention with the long continuous and uninterrupted interstices 34 is ideally suited to permit the bone cement to completely fill the interstices and any gaps between the preapplied cement mantle 30 and the metal surface of the stem 11.

Referring now to FIGS. 6–8, there is shown an additional embodiment in which there is provided a preapplied cement mantle 50 having an integral centralizer 51 and having six interstices 52, two on the side as viewed in FIG. 6 and the side opposite and one on the edge as viewed in FIG. 7 and the edge opposite. As can be appreciated these interstices 52 are significantly larger than the interstices 34 of the previous embodiment. As in the previous embodiment, there is a continuous band 53 of PMMA at the distal end adjacent the integral centralizer 51 and a continuous band 54 adjacent the proximal end 55.

Referring now to FIGS. 9–11, there is shown a further embodiment of preapplied cement mantle 60 which is intended to minimize the occurrence of gaps between the preapplied cement mantle and the metal prosthesis to which it is fitted. The preapplied cement mantle 60 extends from a distal end 61 slightly spaced from the distal end 12 of the stem 11 of the hip joint prosthesis 10 to a proximal end 62 adjacent the enlarged shoulder 16. The preapplied cement mantle 60 is shown as having two interstices 63 on the side viewed in FIG. 9 and two on the side opposite and one on the end viewed in FIG. 10 and one on the side opposite for a total of six interstices which extend throughout a major length of the preapplied cement mantle.

As in the previous embodiments a continuous band 65 of PMMA is adjacent the distal end 61 and a continuous band 66 of PMMA is adjacent the proximal end. However, in molding the preapplied cement mantle 60 of this embodiment, it is formed such that a major portion of the length between the distal end 61 and the proximal end 62 has a reduced cross-sectional size from that which is intended upon application to the femoral stem. In other words, the cross-sectional size of those portions of the preapplied cement mantle 60 in the central areas of the interstices 63 are smaller than the cross-sectional size of the stem 11 to which the preapplied cement mantle is to be affixed. As a result, in an area of the cement mantle 60 about midway between the distal end 61 and proximal end 62, the elongated webs 67 between the interstices 63 are slightly collapsed in the "as molded" condition. Thus, when the preapplied cement mantle 60 is then fitted over the stem 11 those portions of the webs 67 will be urged outwardly by the metal surface of the stem. This is shown schematically in FIG. 11 by the arrows indicated at 68. As a result of this construction, the elongated webs 67 will be urged snugly into contact with the metal surface of the stem 11 following application of the preapplied cement mantle 60 thereto. As previously mentioned, there is no mechanical or chemical bonding between the preapplied cement mantle 60 and the stem 11.

I claim:

1. A cement mantle adapted for use with a femoral hip joint prosthesis having an elongated stem having a length extending from a proximal end to a distal end, said stem tapering from larger to progressively smaller cross-sectional sizes from said proximal end to said distal end, said cement mantle comprising a wall extending from a lower end of relatively small cross-sectional size to an upper end of greater cross-sectional size, a plurality of elongated interstices extending uninterruptedly from a first end adjacent but spaced from said upper end to a second end spaced from said lower end, said interstices tapering from a greater breadth at said first end to a lesser breadth at said second end, at least some of said interstices having a length greater than one-half the distance of the length of said stem.

2. The cement mantle of claim 1, wherein said interstices have a breadth of at least 2 mm at said second end.

3. The cement mantle of claim 1, wherein said interstices define a plurality of longitudinally extending webs, said webs cooperating to define cross-sectional configurations of varying sizes of smaller at said second end to larger at said first end, the cross-sectional size defined by said webs in a plane extending midway between said upper end and said lower end being smaller than the cross-sectional size of said stem in the area to be contacted thereby, said webs being capable of being urged outwardly to a larger cross-sectional size upon engagement of said cement mantle to said stem.

* * * * *